United States Patent [19]

Ruszala

[11] 4,410,727
[45] Oct. 18, 1983

[54] OXYDEHYDROGENATION OF ISOBUTYRIC ACID AND ITS LOWER ALKYL ESTERS

[75] Inventor: Ferdinand A. Ruszala, Columbus, Ohio

[73] Assignee: Ashland Oil, Inc., Ashland, Ky.

[21] Appl. No.: 355,828

[22] Filed: Mar. 8, 1982

[51] Int. Cl.³ .................... C07C 51/377; C07C 57/05; C07C 67/317; C07C 69/54
[52] U.S. Cl. .................................. 562/599; 560/214; 502/213
[58] Field of Search ...................... 562/599; 560/214; 252/435, 437; 260/405.5

[56] References Cited

U.S. PATENT DOCUMENTS 3,948,959  4/1976  Cavaterra et al. ................. 562/599

FOREIGN PATENT DOCUMENTS 52-39622  3/1977  Japan .................................. 562/599

*Primary Examiner*—Vivian Garner
*Attorney, Agent, or Firm*—John F. Jones

[57] ABSTRACT

Isobutyric acid or a lower alkyl ester thereof is oxidatively dehydrogenated in the vapor phase to produce the corresponding alpha, beta-olefinically unsaturated derivative by contact with a heterogeneous catalyst in the presence of oxygen. The catalyst has the empirical formula $Fe^{II}Fe_2^{III}(PO_4)_2 \cdot (OH)_2$ which can exist in the form of Barbosalite and/or Lipscombite.

5 Claims, No Drawings

OXYDEHYDROGENATION OF ISOBUTYRIC ACID AND ITS LOWER ALKYL ESTERS

BACKGROUND OF THE INVENTION

1. Field of the Invention

This invention relates to a novel catalyst for use in the conversion of isobutyric acid or its equivalents and lower alkyl esters thereof correspondingly to methacrylic acid or its equivalents and lower alkyl esters thereof.

2. Description of the Prior Art

There exists considerable prior art relating to the oxydehydrogenation of the lower saturated aliphatic monocarboxylic acids to produce the corresponding $\alpha,\beta$-olefinically unsaturated acids. Early work in this area involved thermal, vapor phase oxydehydrogenation of the saturated aliphatic carboxylic acid in the presence of oxygen and iodine. This approach has not been particularly successful from a commercial standpoint. This is understandably so inasmuch as iodine is costly, exhibits extreme corrosivity properties and poses considerable problems in realizing complete recovery of the comparatively large amounts thereof required in the process. The heterogeneous catalyst method for oxydehydrogenation according to the prior art appears to be the more attractive route to the commercial production of $\alpha,\beta$-olefinically unsaturated monocarboxylic acids. The prior art heterogeneous oxydehydrogenation catalysts useful for this purpose include some heteropoly acids, such as phosphomolybdic acid, optionally with tungsten and/or vanadium. Another type of catalyst included in the prior art is iron phosphate.

Iron phosphate when subjected to calcination is a reasonably good catalyst. There is evidence that the presence of certain extrinsic metal components in the preparation of iron phosphate catalysts cause the formation of more active catalysts for the oxydehydrogenation reaction. For instance, U.S. Pat. No. 3,948,959 discloses that an alkali or alkaline earth metal can be the extrinsic metal for this purpose.

SUMMARY OF THE INVENTION

In accordance with this invention, a catalyst is provided for the oxidative dehydrogenation of a saturated aliphatic monocarboxylic acid or lower alkyl ester thereof, such as isobutyric acid or methyl isobutyrate, to the corresponding $\alpha,\beta$-olefinically unsaturated derivative, such as methacrylic acid or methyl methacrylate. The oxydehydrogenation process comprises contacting a heterogeneous catalyst at a temperature in the range of from 300° to 500° C. With a mixture of the saturated aliphatic monocarboxylic acid and molecular oxygen, said catalyst having the empirical formula $Fe^{II}Fe_2^{III}(PO_4)_2(OH)_2$ which can exist in the form of Barbosalite and/or Lipscombite. This catalyst can be readily produced and it produces high selectivities of the desired product and eliminates the need to include either alkali or alkaline earth metals in the usual iron phosphate catalyst shown in the prior art.

DESCRIPTION OF THE PREFERRED EMBODIMENT

The Barbosalite catalyst can be prepared by methods known to those skilled in the art. A convenient method is that of heating aged $Fe_3(PO_4)_2.8H_2O$ with neutral water for a period of time in a confined area. The ageing is preferably conducted at a temperature in the range of 120°-140° C. for several days. The catalyst is preferably conditioned at about 120°-130° C. in air after it is dried and before use in the oxydehydrogenation reaction.

The use of a support or carrier for the catalyst is included in this invention. The support can be included in the catalyst preparation. Typical carrier materials which can be used include silica, alumina, quartz, titania, zirconia, carbon, silicon carbide, diatomaceous earth, etc.

The process can be carried out using the catalyst in the form of a fluidized bed reactor, a stirred tank reactor or in a fixed bed or packed bed reactor or any combination of these types of reactor configurations. Because of the convenience associated with the use of a fixed bed reactor in a small scale operation, such a reactor will be exemplified herein. In the preferred mode of operation the feed to the reactor comprises a pre-heated gaseous mixture of the saturated aliphatic monocarboxylic acid, molecular oxygen, optionally acetone, steam and inert gaseous diluent. A pre-heat temperature in the range of about 300° to 350° C. is customarily used. The oxydehydrogenation reaction can be carried out in the range of from 300° to 500° C.

The mole ratio of molecular oxygen to carboxylic acid or ester in the feed is from 0.1 to 1.5 and more preferably from 0.7 to 0.75 in the case in which the carboxylic acid is isobutyric acid. Although steam is not necessary for the reaction, its presence is desirable in the feed because it is believed to act beneficially as a heat sink and in minimizing combustion of the carboxylic acid or ester to undesirable waste products. The mole ratio of water to carboxylic acid or ester in the feed should be from about 8 to 20.

Another important parameter is the concentration of the carboxylic acid or ester in the feed. It should be present in from 0.1 to 20 mole percent.

From the standpoint of achieving a reasonable throughput combined with an acceptable yield, the concentration of the carboxylic acid in the feed is from about 3–6 mole percent. Concentration of carboxylic acid is controlled to a large degree by the amount of inert gas present. The preferred inert gas or diluent is nitrogen although other inert gases such as carbon dioxide, helium, argon, and the like are suitable. Air is a very convenient source of oxygen plus inert diluent.

Another important parameter is contact time in the oxydehydrogenation process. Contact or reaction time is defined for the purpose of this invention as the catalyst volume divided by the volume of gas feed per second at the reaction temperature. The catalyst volume is the bulk volume occupied by the catalyst in the reactor. The term catalyst in this sense not only includes the Barbosalite form of iron phosphate itself but also includes the support if present. Accordingly, reaction times can range from 0.05 to 3.0 seconds. The reaction is preferably carried out at or near atmospheric pressure although the use of higher pressures up to about 10 atmospheres is contemplated.

This invention is further illustrated in the following specific examples.

EXAMPLE I

Barbosalite, $Fe^{II}Fe_2^{III}(PO_4)_2(OH)_2$, was prepared by autoclaving $Fe_3(PO_4)_2.8H_2O$ for three days at 120°-140° C. In this case 2.43 g. of $Fe_3(PO_4)_2.8H_2O$ in 12.78 g. of water were autoclaved at 125° C. for three days. The resulting powder was isolated by filtration and was dried for an hour at 125° C. A 25 cc. capacity Teflon lined steel autoclave was used in this case.

EXAMPLE II

In a manner similar to that described in Example I 40 g. of $Fe_3(PO_4)_2.8H_2O$ and 250 g. of water were autoclaved at 130° C. for three days. In this case a 500 cc. capacity autoclave of the type described in Example I was used.

EXAMPLE III

Following the procedure of Example II a Barbosalite catalyst was prepared from 70 g. of $Fe_3(PO_4)_2.8H_2O$ and 200 g. of water by autoclaving at 140° C. for three days.

EXAMPLE IV

A series of oxyhydehydrogenation reactions in which isobutyric acid was converted to methacrylic acid were carried out in a fixed bed reactor which was a 2" long ½" in diameter stainless steel tube containing 0.5 g. of catalyst in powdered form. The Barbosalite catalyst was the one described in Example II above. The preheated feed was composed of 336 ml. of isobutyric acid, 20 sccm 1080 ml. of water, and 55 ml. of acetone. The flow rate of the feed through the reactor was 5.7 ml. per hour. The reaction temperature variations and the results obtained are shown in the following table.

TABLE

| Reaction Temperature °C. | % Conversion of Isobutyric acid | % Selectivity to Methacrylic Acid |
| --- | --- | --- |
| 375 | 31.92 | 76.99 |
| 377 | 29.28 | 82.45 |
| 378 | 29.60 | 77.74 |
| 380 | 28.14 | 81.17 |

In all of the above runs the weight hourly space velocity was maintained at 13.

EXAMPLE V

A. The procedure of Example IV was repeated at 382° C. without acetone in the feed and a selectivity of 76.36% to methacrylic acid was achieved.

B. For the purpose of comparison the procedure of Example IV was repeated at 382° C. using $FePO_4$ as the catalyst and no acetone in the feed and a selectivity of only 70.55% to methacrylic acid was obtained.

I claim:

1. In a process for the catalytic conversion of isobutyric acid or a lower alkyl ester thereof to the corresponding alpha, beta-olefinically unsaturated derivative by oxydehydrogenation wherein a catalyst is contacted with a gaseous stream containing said acid or ester and molecular oxygen at a temperature between about 300° C. and 500° C., the improvement comprising using as catalyst a material having the empirical formula $Fe^{II}Fe_2^{III}(PO_4)_2(OH)_2$ which can exist in the form of Barbosalite and/or Lipscombite.

2. The process of claim 1 wherein isobutyric acid is converted to methacrylic acid.

3. The process of claim 2 wherein the catalyst is the Barbosalite form of iron phosphate.

4. The process of claim 3 wherein water is included in the gaseous stream.

5. The process of claim 4 wherein acetone is included in the gaseous stream.

* * * * *